United States Patent [19]

Bulteau et al.

[11] 4,039,672

[45] Aug. 2, 1977

[54] N-(1'-ALLYPYRROLIDINYL 2'-METHYL) 2-METHOXY 4,5-AZIMIDO BENZAMIDE AND ITS PHARMACEUTICALLY ACCEPTABLE SALTS

[75] Inventors: Gerard Bulteau, Paris; Jacques Acher, Itteville; Claude Collignon, Saint Remy-les-Chevreuses; Jean-Claude Monier, Lardy, all of France

[73] Assignee: Societe d'Etudes Scientifiques et Industrielles de l'Ile-de-France, Paris, France

[21] Appl. No.: 554,612

[22] Filed: Mar. 3, 1975

[30] Foreign Application Priority Data

Jan. 11, 1975  Germany ............................... 2500919
Jan. 31, 1975  France ................................... 75.3005

[51] Int. Cl.² ................... C07D 249/18; A61K 31/41

[52] U.S. Cl. .............................. 424/269; 260/308 R; 260/308 D; 260/349; 260/465 D; 260/471 R; 260/519; 260/543 R; 260/546; 260/558 H

[58] Field of Search ..................... 260/308 B; 424/269

[56] References Cited

U.S. PATENT DOCUMENTS 3,839,330  10/1974  Thominet ........................ 260/308 B

*Primary Examiner*—Raymond V. Rush
*Attorney, Agent, or Firm*—Frank M. Nolan

[57] ABSTRACT

The azimido benzamide of this invention and its pharmaceutically acceptable salts have an unusually and unexpectedly high therapeutic index and low toxicity in the treatment of emesis in mammals. Pharmacological testing demonstrated the superior efficacy of the compound of this invention over known, similar compounds.

5 Claims, No Drawings

N-(1'-ALLYPYRROLIDINYL 2'-METHYL) 2-METHOXY 4,5-AZIMIDO BENZAMIDE AND ITS PHARMACEUTICALLY ACCEPTABLE SALTS

This invention relates to N-(1'-allylpyrrolidinyl 2'-methyl) 2-methoxy 4,5-azimido benzamide, its pharmaceutically acceptable salts, processes of producing said compound and methods of using the compound and/or salts thereof for the protection of mammals against emesis. The compound of this invention may be in the levo or dextro form or be a racemic mixture.

The structure of the compound of the invention is represented by the following three tautomeric forms:

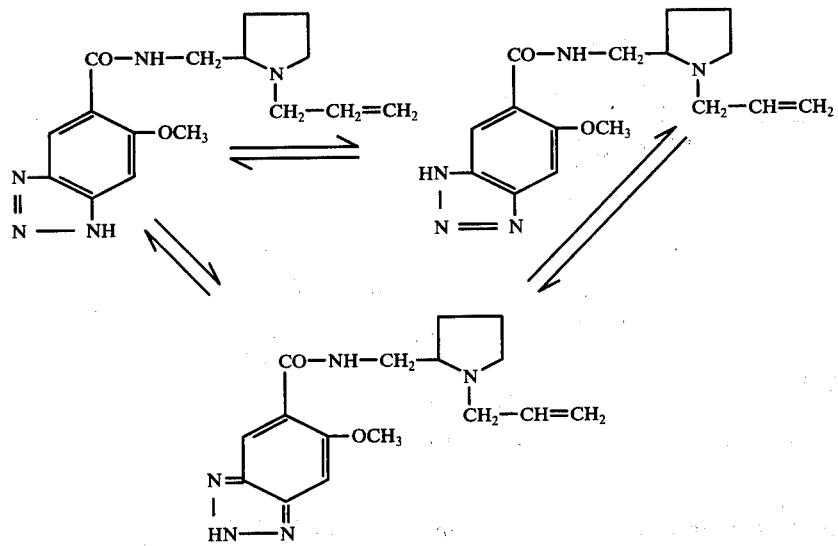

The compound of this invention may be produced by nitrating a 2-methoxy 4-substituted benzoic acid or a reactive derivative thereof, the 2-methoxy 4-substituted benzoic acid having the formula:

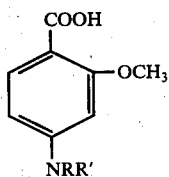

in which R and R' are hydrogen or acyl.

Examples of reactive derivatives of the 2-methoxy 4-substituted benzoic acid are: reactive acid esters such as cyanomethyl ester, methoxymethyl ester, substituted or unsubstituted phenyl esters, acid halogenides such as chlorides or bromides; acid azides; symmetrical anhydrides; mixed anhydrides formed with lower alkyl chloroformates; hydrazides; azolides such as triazolides, tetrazolides, especially imidazolides; acid isocyanates. If a reactive derivative of the 2-methoxy 4-substituted benzoic acid is to be employed, such derivative is desirably an alkyl ester of the acid in which the alkyl group has less than 6 carbon atoms.

The resulting 5-nitro compound is hydrogenated to produce a 5-amino compound. The 5-amino compound is then diazotized. The resulting 4,5-azimido compound is reacted with 1-allyl 2-aminomethyl pyrrolidine, or reactive derivatives.

The reaction may be achieved by nitration of a lower alkyl ester of 2-methoxy 4-amino benzoic acid, by hydrogenation of the resulting alkyl 2-methoxy 4-amino 5-nitro benzoate, diazotization of the resulting alkyl 2-methoxy 4,5-diamino benzoate and amidation of the resulting alkyl 2-methoxy 4,5-azimido benzoate with 1-allyl-2-aminomethyl pyrrolidine.

In the first step of the above process preferably methyl 2-methoxy 4-amino benzoate is employed. Other lower alkyl esters, such as ethyl, propyl, butyl or pentyl esters, however, may be used as well.

The hydrogenation of the nitro group may be achieved either by means of hydrogen in presence of catalysts, such as platinum, palladium or Raney nickel, or by nascent hydrogen with metals in the presence of strong acids such as Fe/HCl or Sn/HCl or Zn/HCl, as well as by other hydrogenation agents.

The 4-5 diamino compound can then be diazotised with a suitable diazotization agent such as NaNO$_2$/HCl or isoamyl nitrite to obtain the corresponding 4,5-azimido compound.

The azimido compound is reacted with 1-allyl 2-aminomethyl pyrrolidine, either in the presence or absence of inert solvents such as alcohols, polyols, benzene, toluene, dioxane, chloroform, diethyleneglycol, dimethylether. It is also possible to use an excess of the amine as a solvent. It may be preferable to heat the reaction mixture during amidation, up to the boiling point of the above solvents.

The reaction may be conducted by starting from a lower alkyl ester of 2-methoxy 4-acylamino benzoic acid. Instead of the acetyl group preferably employed for substituting the amino function in the 4th position of the above starting material, other easily cleavable groups such as formyl, propionyl, butyryl, alkoxycarbonyl, phthaloyl or benzoyl may be used.

The above reaction may also be achieved by cleavage of the acyl group before hydrogenation of the nitro group. The resulting 4,5-diamino compound can then be further reacted as described above.

If the acyl group is not a phthaloyl group, it may also be cleaved after amidation.

An illustration of the process of the invention is given by the following reaction scheme:

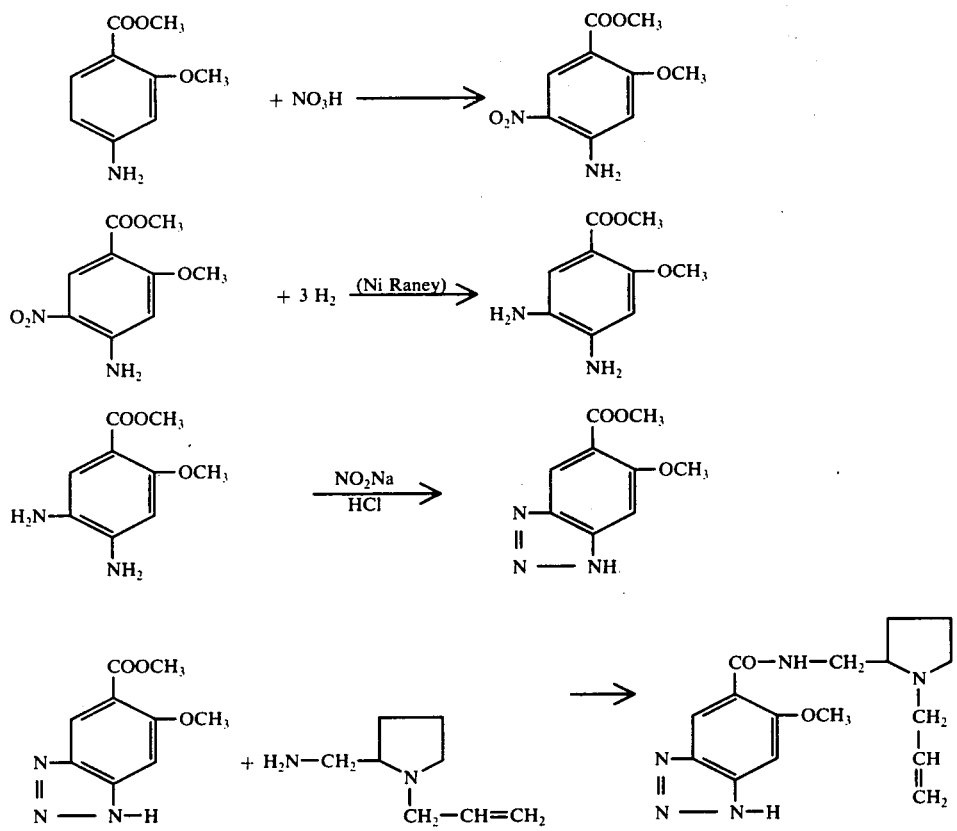

According to the process of the invention, the reaction can be started from the 2-methoxy 4-amino benzoic acid which can be nitrated, the formed 2-methoxy 4-amino 5-nitro benzoic acid hydrogenated, the formed 2-methoxy 4,5-diamino benzoic acid diazotised, the thus obtained 2-methoxy 4,5-azimido benzoic acid reacted either with a reactive derivative of 1-allyl-2-aminomethyl pyrrolidine or in the form of one of its reactive derivates with 1-allyl-2-aminomethyl pyrrolidine. The N-(1'-allylpyrrolidinyl-2' methyl) 2-methoxy 4,5-azimido benzamide is obtained.

The same synthetic route may be followed when a 2-methoxy 4-acylamino benzoic acid or an alkyl ester is employed as the starting material. For example, when the starting material is 2-methoxy 4-acylamino benzoic acid, the 2-methoxy 4-acetylamino benzoic acid is nitrated. The resulting 2-methoxy 4-acetylamino 5-nitro benzoic acid is successively hydrogenated and diazotized in the manner described above. Finally the resulting diazotized product is reacted with either 1-allyl-2-aminomethyl pyrrolidine or a reactive derivative thereof. The resulting reaction product is deacylated, without isolation, if desired.

The deacylation may be effected prior to hydrogenation or diazotization. This process step is necessary, for instance, in the case of 4-phthaloylamino substitutions. In the above described synthetic route, the following products may be employed as reactive derivatives of the amine: Reaction products of the amine with phosphorus chloride, phosphorus oxychloride, dialkyl — or diaryl or orthophenylene chlorinated phosphites, alkyl — or aryl dichlorinated phosphites or 1-allyl pyrrolidinyl 2-methyl isothiocyanate. Such reactive derivatives may be reacted with the acid with or without prior isolation.

Furthermore it is also possible to react the free acid and the free amine in the presence of a condensation agent: for example, a carbodiimide such as dicyclohexyl carbodiimide, silicon tetrachloride, phosphoric anhydride.

The compound obtained by the process of the invention may be reacted with pharmaceutically acceptable inorganic or organic acids, such as hydrogen chloride, hydrogen bromide, sulfuric acid, phosphoric acid, oxalic acid, acetic acid, tartaric acid, citric acid, methane sulfonic acid, to form acid addition salts of the compound. The quaternary ammonium salts of the compound may be obtained by reacting the compound with a pharmaceutically acceptable aliphatic or aromatic alkylating agent such as methyl chloride, methyl bromide, dimethyl sulfate, or methyl p-toluenesulfonate.

For therapeutic purposes the compound of the invention may be employed in the form of a pharmaceutically acceptable acid addition salt along with pharmaceutically common auxiliary substances and/or dilution agents in the form of tablets, dragees, solutions for injection, syrups, or in any other suitable form. The compound of this invention, with or without other therapeutic ingredients or adjuvents, may be administered in convenient dosage forms. The daily dosage may vary over wide limits for the treatment of emesis as determined by the veterinarian or physician.

Pharmacological tests show that the compound of the invention, referred to as compound A hereafter, shows superior properties with respect to its antiemetic and cataleptic effectiveness at comparably low toxicities when compared with several recognized benzamides known to have excellent effectiveness. The following compounds were used for comparative testing:

1. N,N-diethylaminoethyl-2-methoxy 4-amino 5-chloro benzamide (compound B) commercialized under the generic name "Metoclopramide"
2. N-(1-ethyl 2-pyrrolidinylmethyl) 2-methoxy 4,5-azimido benzamide (Compound C) as described in Example 2 of U.S. Pat. No. 3,839,330

The following experimental results were obtained:

A. Toxicity ($DL_{50}$, mg/kg, i. v., 5 days, mice)

| Compound | $DL_{50}$ |
| --- | --- |
| A | 92.7 |
| B | 38 |
| C | 69.2 |

B. Antiemetic activity ($DE_{50}$, s. c., dogs)

| Emesis induced by | A | B | C | |
| --- | --- | --- | --- | --- |
| Apomorphine | 5.4 | 26.8 | 14 | µg/kg |
| Hydergine | 63 | 207 | — | µg/kg |
| Cupric sulfate | 0.99 | 0.92 | — | mg/kg |
| Lanatoside | 1.3 | 4.5 | — | mg/kg |

C. Therapeutic index $$J = \frac{DL_{50}, \text{i. v., Mice}}{DE_{50}, \text{s. c., Dogs}}$$

| Compound | J |
| --- | --- |
| A | $160 \times 10^2$ |
| B | $14 \times 10^2$ |
| C | $49 \times 10^2$ |

D. Cataleptic activity ($DE_{50}$, s. c., mg/kg)

| Compound | $DE_{50}$ |
| --- | --- |
| A | 10% at 200 mg/kg |
| B | 30.8 |
| C | 84.8 |

Thus the compound of the invention exhibits a strikingly improved therapeutic index over the comparison compounds, with reduced cataleptic activity.

A more comprehensive understanding of this invention is obtained by reference to the following examples:

EXAMPLE I

Stage 1: Methyl 2-methoxy 4-amino 5-nitro benzoate 72.5 g (0.4 mol) methyl 2-methoxy 4-amino benzoate, 140 ml acetic acid and 126 g acetic anhydride are introduced into a 2 liter flask equipped with stirrer, thermometer and dropping funnel. The mixture is warmed to about 40° C for 30 minutes. 48 ml nitric acid ($d = 1.49$) are added drop by drop by means of the dropping funnel. The addition of nitric acid being terminated, stirring is continued for 2 hours at 40° C. Then the mixture is poured into 600 ml of a methanol solution of sulfuric acid (0.4 mol). The mixture is then stirred. Then 1600 ml of water and ice are added. The formed crystals are filtered with suction.

55.2 g (yield 61%) of methyl 2-methoxy 4-amino 5-nitro benzoate having a melting point of 214° C are obtained.

Stage 2: Methyl 2-methoxy 4,5-diamino benzoate 555 g of methyl 2-methoxy 4-amino 5-nitro benzoate, 2500 ml of methanol and 300 g of Raney nickel are introduced into a 5 liter autoclave.

Hydrogen is applied with a pressure of 50 kg. The temperature rises to 50° C and is maintained during the entire absorption. After cooling, nickel is removed by filtration and washed with methanol. The solvent is removed under reduced pressure. The formed crystals are washed two times with 600 ml of water and dried at 50° C.

305 g (yield 63.5%) of methyl 2-methoxy 4,5-diamino benzoate, having a melting point of 139°-140° C are obtained.

Stage 3: Methyl 2-methoxy 4,5-azimido benzoate 294 g (1.5 mol) of methyl 2-methoxy 4,5-diamino benzoate, 2500 ml of water, 550 ml of hydrochloric acid ($d = 1.18$ are introduced into a 5 liter flask equipped with stirrer, thermometer and dropping funnel. The mixture is cooled to 0°-5° C and a solution of 108 g of sodium nitrite in 500 ml of water is added dropwise. The mixture is heated to 35° C for 30 minutes, and then cooled. The resulting crystals are filtered, washed three times with 300 ml of methylene chloride, and once with water. After drying at 30° C, 256 g (yield 82.4%) of methyl 2-methoxy 4,5-azimido benzoate having a melting point of 190°-192° C are obtained.

Stage 4: N-(1'-allylpyrrolidinyl 2'-methyl) 2-methoxy 4,5-azimido benzamidehydrochloride 621 g of methyl 2-methoxy 4,5-azimidobenzoate, 3 liters of anhydrous toluene and 425 g of amine are introduced into a 6 liter three-necked flask equipped with sealed mechanical stirrer, thermometer and ascending reflux condenser. The mixture is held under reflux conditions for 5 hours.

The mixture is cooled to 50° C after which 600 ml of a solution of 350 g of hydrogen chloride in 1 liter of ethanol are added. The temperature rises to 70°-80° C. The mixture is cooled to 50° C, after which the toluene layer is separated from an oily residue and the oily residue is taken up in 3 liters of methanol. The mixture is warmed until a complete dissolution is obtained. This solution is filtered at its boiling temperature with 150 g of charcoal (3 S).

6 liters of methyl ethyl ketone are added to the filtrate, after which the mixture is cooled to 0° C. The benzamide crystallizes slowly. It is filtered by suction and washed with 500 ml of methyl ethyl ketone in two portions. It is then dried at 50° C in a ventilated dryer.

687 g (yield 65%) of N-(1'-allylpyrrolidinyl 2'-methyl) 2-methoxy 4,5-azimido benzamide hydrochloride having a melting point of 206°-208° C are obtained.

HCL%: theory: 10.38. found: 10.18.
Purity in non aqueous medium with HCl $O_4$: 99.5%

EXAMPLE II

Stage 1: Methyl 2-methoxy 4-acetylamino 5-nitro benzoate 223 g (1 mol) of methyl 2-methoxy 4-acetylamino benzoate, 350 ml of acetic acid and 337 g of acetic anhydride are introduced into a 2 liter flask equipped with stirrer, thermometer and dropping funnel. The mixture is warmed to about 40° C, whereby a clear solution is obtained. It is then cooled to 15°-20° C, after which 106 g (1.5 mol) of nitric acid ($d = 1.49$) are added drop by drop by means of the dropping funnel. The addition of nitric acid being terminated, stirring is continuted for ½ hour at 40° C. Then the mixture is cooled and poured into 5 liters of water.

182 g (yield 68%) of methyl 2-methoxy 4-acetylamino 5-nitro benzoate, having a melting point of 163°-165° C are obtained.

Stage 2: Methyl 2-methoxy 4-acetamino 5-amino benzoate hydrochloride 1 kg of methyl 2 -methoxy 4-acetamino 5-nitro benzoate, 3 liters of ethyl acetate and 3 spoonfuls of Raney nickel are introduced into a 5 liter autoclave.

The mixture is warmed to 75° C with stirring. Then hydrogen gas is applied with a pressure of 50 kg. The reduction reaction starts quickly. For cooling purposes, the reaction vessel is ventilated. The temperature rises to 95° C. This temperature is maintained during the entire absorption. The total absorption takes ten minutes. The hydrogen gas is recharged four to five times in equal manner until the absorption ceases.

The reaction is carried out within 1 hour and 15 minutes. After cooling, nickel is removed by filtration and washed with 100 ml of ethyl acetate. The filtrate is acidified with 500 ml of a solution containing 350 g of hydrogen chloride in 1000 ml of ethanol. The hydrochloride crystallizes.

It is filtered with suction at 15° C and washed with 500 ml of ethyl acetate. It is dried in a ventilated dryer at 50° C.

905 g product (yield 88%) with a melting point of 202°–205° C are obtained.

Stage 3: 1-Acetyl 5-carbomethoxy 6-methoxy benzotriazole 14 liters of water and 1920 g of hydrochloride of 2-methoxy 4-acetamino 5-amino benzoate are introduced into a 20 liter reaction vessel equipped with mechanical stirrer, thermometer and dropping funnel and which is suitably mounted to allow cooling by means of a cooling bath.

The hydrochloride is dissolved completely with stirring.

700 ml of hydrochloric acid are added at once. Thereafter a solution of 490 g sodium nitrite in 1 liter of water is added drop by drop within about 1 hour at a temperature between 25° and 30° C. The azimido compound crystallizes according to its formation.

The above addition being terminated, stirring is continued for 1 hour at 25° C.

The azimido compound is filtered by suction and washed several times with water. It is dried in a ventilated dryer at 30° C.

1485 g (yield 85%) of product with a melting point of 114°–115° C are obtained.

Stage 4: Methyl 2-methoxy 4,5-azimido benzoate 7.4 liters of methanol and 1485 g of 1-acetyl 5-carbomethoxy 6-methoxy benzotriazole are introduced into a 20 liter reaction vessel equipped with a sealed mechanical stirrer, ascending reflux cooler and dropping funnel.

The mixture is warmed with stirring to the reflux temperature. Then 460 ml of hydrochloric acid are added. Complete dissolution occurs. Then 100 g charcoal (3S) are added, and reflux conditions are maintained for 20 minutes.

The charcoal is filtered off from the hot mixture. The latter is cooled to 0° C, resulting in crystallization of the azimido ester. It is filtered by suction, washed several times with water and dried in a ventilated dryer at 50° C.

780 g (yield 63%) of product are obtained.

The product is purified by dissolving 780 g of azimido ester in a solution of 1 liter of concentrated ammonia in 3.9 liters of water followed by the addition of 100 g of charcoal. The mixture is then allowed to stand for ten minutes, after which is it filtered.

The filtrate is acidified with hydrochloric acid up to a pH of 1. The azimido ester crystallizes. It is filtered by suction and washed several times with water.

The moist product is again dissolved in a solution of 1 liter of ammonia in 3.9 liters of water and filtered with 100 g of charcoal.

The azimido compound is precipitated at a pH of 1 with hydrochloric acid. It is filtered with suction, washed with water and dried in a ventilated dryer at 50° C.

742 g (total yield 60%) of the colorless product, with a melting point of 192° C are obtained.

Stage 5: N-(1'-allylpyrrolidinyl-2'-methyl) 2-methoxy 4,5-azimido benzamide hydrochloride 621 g of methyl 2-methoxy 4,5-azimido benzoate, 3 liters of anhydrous toluene and 425 g of amine are introduced into a 6 liter three-necked flask equipped with sealed mechanical stirrer, thermometer and ascending reflux condenser. The mixture is held under reflux conditions for 5 hours.

The mixture is cooled to 50° C, after which 600 ml of a solution of 350 g of hydrogen chloride in 1 liter of ethanol are added. The temperature rises to 70°–80° C. The mixture is cooled to 50° C, after which the toluene layer is separated from an oily residue.

The oily residue is taken up in 3 liters of methanol. The mixture is warmed until a complete dissolution is obtained. This solution is filtered at its boiling temperature with 150 g of charcoal (3S).

6 liters of methyl ethyl ketone are added to the filtrate, after which the mixture is cooled to 0° C. The benzamide crystallizes slowly. It is filtered by suction and washed with 500 ml of methyl ethyl ketone in two portions. After this it is dried at 50° C in a ventilated dryer.

687 g (yield 65%) of N-(1'-allylpyrrolidinyl-2'-methyl) 2-methoxy 4,5-azimido benzamide hydrochloride having a melting point of 206°–208° C are obtained.

HCL%: theory: 10.38. found: 10.13.

Purity in non aqueous medium with HCl O$_4$: 99.5

EXAMPLE III

Stage 1: 2-Methoxy 4-amino 5-nitro benzoic acid

As above described 16.7 g (0.1 mol) of 2-methoxy 4-amino benzoic acid were nitrated.

13.8 g (yield 64.9%) of 2-methoxy 4-amino 5-nitro benzoic acid having a melting point of 254° C were obtained.

Stage 2: 2-Methoxy 4,5-diamino benzoic acid

As above described, 28 g (0.13 mol) of 2-methoxy 4-amino 5-nitro benzoic acid were hydrogenated and 19.8 g of 2-methoxy 4,5-diamino benzoic acid were produced (yield 83.6%).

Stage 3: 2-Methoxy 4,5-azimido benzoic acid 36.4 g (0.2 mol) of 2-methoxy 4,5-diamino benzoic acid were treated as above described by sodium nitrite in the presence of hydrochloric acid. 31 g (yield 80.3%) of 2-methoxy 4,5-azimido benzoic acid having a melting point of 245° C were obtained.

Stage 4: N-(1-allyl 2-pyrrolidylmethyl) 2-methoxy 4,5-azimido benzamide 38.6 g (0.2 mol) of 2-methoxy 4,5-azimido benzoic acid were dissolved in anhydrous toluene and 56 g (0.4 mol) of 1-allyl 2-amino-methyl pyrrolidine were added. The mixture was heated to 50° C and then 42 g (0.3 mol) of phosphoric anhydride were added. The mixture was warmed at reflux temperature for 3 hours and then cooled to 80° C. After adding water, the aqueous layer was alkalized. The crystals were filtered, washed with water and then dissolved in 450 ml of acetone. After crystallization, the product was filtered, washed and dried.

40.4 g (yield 65%) of N-(1'-allyl 2'-pyrrolidylmethyl) 2-methoxy 4,5-azimidobenzamide having a melting point of 139° C were obtained.

EXAMPLE IV

Stage 1: 2-Methoxy 4-acetylamino 5-nitro benzoic acid

In the same manner described above, 20.9 g (0.1 mol) of 2-methoxy 4-acetylamino benzoic acid were nitrated.

16.5 g (yield 64.9%) of 2-methoxy 4-acetylamino 5-nitro benzoic acid having a melting point of 186°–188° C were obtained.

Stage 2: 2-Methoxy 4-acetylamino 5-amino benzoic acid

In the manner described above, 32 g (0.13 mol) of 2-methoxy 4-acetylamino 5-nitro benzoic acid were hydrogenated and 24.5 g (yield 84%) of 2-methoxy 4-acetylamino 5-amino benzoic acid were obtained.

Stage 3: 1-Acetyl 5-hydroxycarbonyl 6-methoxy benzotriazole 8.7 g (0.039 mol) of 2-methoxy 4-acetylamino 5-amino benzoic acid were treated in the same manner as described, by sodium nitrite in the presence of hydrochloric acid.

7.3 g (yield 79.6%) of 1-acetyl 5-hydroxycarbonyl 6-methoxy benzotriazole having a melting point of 208°–212° C were obtained.

Stage 4: 1-Acetyl 5-chlorocarbonyl 6-methoxy benzotriazole 4.7 g of 1-acetyl 5-hyroxycarbonyl 6-methoxy benzotriazole, 16.5 ml of thionyl chloride and 11 ml of chloroform are introduced into a 250 ml flask. The mixture is heated to the reflux temperature for 30 minutes. After cooling, the solvents are removed under reduced pressure.

4.7 g (yield 92.7%) of 1-acetyl 5-chlorocarbonyl 6-methoxy benzotriazole having a melting point of 170° C are obtained.

Stage 5: N-(1'-allyl 2'-pyrrolidylmethyl) 2-methoxy 4,5-azimidobenzamide hydrochloride 2.2 g (0.016 mol) of 1-allyl 2-aminomethyl pyrrolidine and 28 ml of methyl ethyl ketone are introduced into a 250 ml flask. Then 3.8 g (0.015 mol) of 1-acetyl 5-chlorocarbonyl 6-methoxy benzotriazole are added. The mixture is allowed to stand overnight. The solvent is removed under reduced pressure. 5 ml of hydrochloric acid ($d=1.18$) and 28 ml of ethyl alcohol are added and the mixture is heated to the reflux temperature for 30 minutes. After cooling, the solvent is removed under reduced pressure, and the residue is dissolved in boiling dimethyl formamide. The mixture is filtered, and after cooling, the benzamide crystallizes. The crystals are filtered by suction, washed with some dimethylformamide, then with tetrahydrofuran, and are dried at 50° C.

3.2 g (yield 60.7%) of N-(1'-allyl-2'-pyrrolidylmethyl) 2-methoxy 4,5-azimido benzamide hydrochloride having a melting point of 206° C are obtained.

HCl%: theory: 10.38. found: 10.27.

What is claimed is:

1. A compound selected from the class consisting of N-(1'-allylpyrrolidinyl-2'-methyl)-2-methoxy-4,5-azimidobenzamide, pharmaceutically acceptable acid addition salts thereof and pharmaceutically acceptable quaternary ammonium salts thereof.

2. A compound of claim 1 which is N-(1'-allylpyrrolidinyl-2'-methyl)-2-methoxy-4,5-azimidobenzamide.

3. A compound of claim 1 in which a pharmaceutically acceptable acid addition salt of N-(1'-allylpyrrolidinyl 2'-methyl) 2-methoxy 4,5-azimidobenzamide.

4. A method of protecting a mammal against emesis which comprises administering to said mammal an anti-emesis effective amount of a compound of claim 1.

5. A compound of claim 1 which is a pharmaceutically acceptable quaternary ammonium salt of N-(1'-allylpyrrolidinyl-2'-methyl)-2-methoxy-4,5-azimidobenzamide.

* * * * *